United States Patent [19]

Tsurutani et al.

[11] Patent Number: 5,204,107
[45] Date of Patent: Apr. 20, 1993

[54] SLOW-RELEASING COMPOSITION OF PLATINUM-CONTAINING ANTICANCER AGENT

[75] Inventors: Ryoichi Tsurutani; Koji Kifune; Yuriko Nakamura, all of Kyoto, Japan

[73] Assignee: Unitika Ltd., Hyogo, Japan

[21] Appl. No.: 794,909

[22] Filed: Nov. 20, 1991

[30] Foreign Application Priority Data

Nov. 20, 1990 [JP] Japan ................................ 2-316409

[51] Int. Cl.$^5$ .......................... A61K 9/00; A61K 9/16; A61K 31/73; A61K 47/00
[52] U.S. Cl. ..................................... 424/426; 424/422; 424/488; 424/493; 424/499; 514/55; 536/20
[58] Field of Search .............................. 424/422–426, 424/488, 493, 499; 536/20; 514/55

[56] References Cited

U.S. PATENT DOCUMENTS

| | | | |
|---|---|---|---|
| 4,419,340 | 12/1983 | Yolles | 424/19 |
| 4,612,009 | 12/1986 | Drobnik et al. | 604/891 |
| 4,873,092 | 10/1989 | Azuma et al. | 424/499 |

FOREIGN PATENT DOCUMENTS

| | | |
|---|---|---|
| 331504 | 9/1989 | European Pat. Off. |
| 59-027826 | 2/1984 | Japan |
| 61-197529 | 9/1986 | Japan |
| 1-061429 | 3/1989 | Japan |
| 1-252602 | 10/1989 | Japan |
| 1-252603 | 10/1989 | Japan |

OTHER PUBLICATIONS

Nishioka et al. (I), C.A. 112:62514k (1990).
Nishioka et al. (II), C.A. 114:49479z (1991).
Devrvoo et al. C.A. 114:128893h (1991).
Unitaka C.A. 103:11458b (1985) of JPN 60 36410, 25 Feb. 1985.
Okamoto et al. C.A. 104:174551m (1986).
Yolles et al. C.A. 90:157040u (1979).
Los et al. C.A. 115:247615z (1991).
STN International Information Services Data Base: Chemical Abstracts, vol. 106, No. 14, abstract No. 107939x, Columbus, Ohio, US.
Data Base: WPIL, accession No. 89-117247 [16], Derwent Publications Ltd.

Primary Examiner—Shep K. Rose
Attorney, Agent, or Firm—Sughrue, Mion, Zinn, Macpeak & Seas

[57] ABSTRACT

A slow-releasing composition of a platinum-containing anticancer agent comprising a platinum-containing anticancer agent bound to deacetylated chitin. The release of the platinum-containing anticancer agent is sustained for a prolonged duration of several months, thereby minimizing undesirable side effects of the platinum-containing anticancer agent.

13 Claims, No Drawings

SLOW-RELEASING COMPOSITION OF PLATINUM-CONTAINING ANTICANCER AGENT

FIELD OF THE INVENTION

This relates to a slow-releasing platinum-containing anticancer composition comprising a platinum-containing anticancer agent bound to deacetylated chitin.

BACKGROUND OF THE INVENTION

Of various known anticancer agents, cisdiaminedichloroplatinum (II) (Cisplatin TM) now is preferred because of its broad antitumor effects. However, Cisplatin TM also has strong toxicity causing side effects, such as nephrotoxicity, disturbances of hematopoietic organs, and disturbances of auditory nerves. Cis-diamine(1,1cyclobutanedicarboxylato)platinum (II) (Carboplatin TM) was developed for the purpose of reducing the side effects of Cisplatin without weakening its antitumor activity. However, Carboplatin has been reported to still have strong side effects such as nausea, vomiting, and anorexia, as is usual with anticancer agents.

Presently, such platinum-containing anticancer agents are administered alone. There are no cases reported in which such a platinum-containing anticancer agent is supported on a high-molecular weight compound so as to suppress the side effects.

On the other hand, in order to inhibit manifestation of unfavorable side effects of a drug, it has been attempted to minimize the concentration of the drug. One of the approaches is to incorporate a drug into a synthetic high-molecular weight polymer so that the release of the drug may be sustained by the membrane function of the synthetic high-molecular weight polymer. The thus sustained release usually has a duration of from 2 to 3 days. However, use of a synthetic high polymer as a carrier for a drug carries the risk of side effects arising from accumulation of the synthetic high polymer in the living body.

To avoid the risk, use of chitin in an acetylated form, a biodegradable natural high-molecular weight compound, as a carrier for a drug is attracting attention (see Ogawa Kozo, et al., Chitin-Chitosan no Oyo (edited by Chitin-Chitosan Kenkyukai) (1990)). The inventors of the present invention previously proposed a process for preparing a slow-releasing composition releasing a drug for a prolonged duration by using chitin in an acetylated form obtained from crustaceans, e.g., crabs and lobsters, in a molded form as disclosed in JP-A-61-268616 (the term "JP-A" as used herein means an "unexamined published Japanese patent application"). The proposed slow-releasing composition, however, was still unsatisfactory in practice, though successful in reducing the residual carrier substance in a living body and extending the duration of drug release.

SUMMARY OF THE INVENTION

An object of the present invention is to provide a slow-releasing composition of a platinum-containing anticancer agent which slowly releases a platinum-containing anticancer agent, e.g., Cisplatin TM and Carboplatin TM, with reduced side effects for a prolonged duration of several months that has never been reached.

In the course of studies on sustained release of an anticancer agent by using a chitin molded form, the inventors found a surprising fact that a platinum-containing anticancer agent, such as Cisplatin TM and Carboplatin TM, firmly binds to deacetylated chitin, and the composition does not release the platinum-containing anticancer agent under usual conditions in physiological saline and even under severe conditions such as in a hydrochloric acid-acidic environment. It has also been found that the composition slowly releases the platinum-containing anticancer agent for a prolonged duration in the presence of lysozyme. The present invention has been completed based on these findings.

The present invention provides a slow-releasing composition of a platinum-containing anticancer agent comprising a platinum-containing anticancer agent bound to deacetylated chitin.

DETAILED DESCRIPTION OF THE INVENTION

In the slow-releasing platinum-containing anticancer composition of the present invention, the mode of binding of deacetylated chitin to a platinum-containing anticancer agent is not particularly limited. The deacetylated chitin-platinum-containing anticancer agent composition may further contain other components generally used in pharmaceuticals. Further, the slow-releasing composition of the present invention may have any form generally employed for pharmaceuticals, such as a fibrous form, a powder form, etc.

The deacetylated chitin which can be used in the present invention can be prepared in a known manner, for example, by deacetylating chitin in an alkaline aqueous solution or by re-acetylating chitosan with acetic anhydride in methanol.

The degree of deacetylation (hereinafter, "DA") of deacetylated chitin to be used, can be selected from more than about 0 to about 100%, according to a desired duration of release and a desired amount of the platinum-containing anticancer agent to be incorporated. For the purpose of good decomposability in the living body, DA of the deacetylated chitin is preferably from about 30 to about 90%.

Chitin to be deacetylated or chitosan to be re-acetylated may have any form, such as a fibrous form, a sheet form, a film form, a particulate form, a granular form, a powderous form, a spongy form, and a gel form.

The platinum-containing anticancer agents which can be used in the present invention include, e.g., cis-diaminedichloroplatinum (II), cis-diamine(1,1-cyclobutanedicarboxylato)platinum (II), (glycolato-0,0')-diamineplatinum (II), (R)-(−)-2-aminomethylpyrrolidone(1,1-cyclobutanedicarboxylato)platinum (II), cis-1,1cyclobutanedicarboxylato(2R)-2-methyl-1,4-butanediamineplatinum (II), trans-1-diaminocyclohexaneoxalatoplatinum (II), glycolato-3-aminopyrrolidineplatinum (II), cis-dichloro-trans-dihydroxybisisopropylamineplatinum (IV) and lacto-0,0-1,2-bis-(aminomethyl)cyclobutaneplatinum (II).

The content of the platinum-containing anticancer agent in the slow-releasing composition of the present invention preferably ranges from about 5 to about 60% by weight, though varying depending on the form of chitin, the kind of the platinum-containing anticancer agent, and a desired duration of release. If the content of the platinum-containing anticancer agent is too small, administration of the slow-releasing composition is required in a large amount. If it is too much, decomposability of the composition deteriorates in the living body.

Binding of deacetylated chitin and a platinum-containing anticancer agent can be carried out, for example, by dipping deacetylated chitin in a solution of a platinum-containing anticancer agent.

Solvents to be used in the above-described treatment are not limited as long as they are capable of dissolving a platinum-containing anticancer agent. Examples of useful solvents are water, physiological saline, a hydrochloric acid aqueous solution, dimethylformamide, and dimethylacetamide. The reaction temperature is not limited so long as the platinum-containing anticancer agent may be stably present in solution. A preferred reaction temperature is from about 0° to about 60° C., and particularly from about 10° to about 50° C.

Where deacetylated chitin is treated in a non-dissolved state, the solution after completion of the treatment is filtered or centrifuged to collect a deacetylated chitin with platinum-containing anticancer agent. Where deacetylated chitin is treated in a dissolved state, the solution after completion of the treatment is concentrated to dryness or by adding the solution to a poor solvent for deacetylated chitin, e.g., methanol, to recover the composition of any desired form.

An illustrative example of the preparation of a slow-releasing platinum-containing anticancer composition is described below using a powder form.

Chitin is dissolved in an appropriate solvent. The resulting dope is extruded through a nozzle having fine holes, solidified in a solidifying medium, e.g., isobutanol, and taken out on a roller to obtain chitin fibers (wet spinning method). The chitin fibers are then deacetylated in a 28 wt % sodium hydroxide aqueous solution at 121° C. for 1 hour to obtain deacetylated chitin fibers having a DA of 60%. The fibers are cut to several millimeters and ground in a ball mill to a powder having a particle size of about 10 μm. The powder is immersed in physiological saline having dissolved therein Cisplatin TM at 30° C. for 10 hours. After the binding reaction, the reaction mixture is subjected to centrifugal separation to obtain a slow-releasing platinum-containing anticancer composition comprising a deacetylated chitin and Cisplatin TM.

The slow-releasing platinum-containing anticancer composition according to the present invention does not release the platinum-containing anticancer agent even under severe conditions such as in a hydrochloric acid-acidic environment still less under general conditions such as in physiological saline until it is in the presence of lysozyme. This demonstrates that the platinum-containing anticancer agent is slowly released from the composition in a living body where lysozyme acts. Therefore, the composition of the present invention has a very useful function demanded for slow-releasing compositions and reduces the side effects of the platinum-containing compound.

There is no limitation in application form of the slow-releasing composition according to the present invention in clinical use. For example, after excision of cancer such as esophageal carcinoma and gastric cancer, the slow-releasing composition according to the present invention can be placed around the operated portion for the purpose of cancer-recurrent prevention, in the form of fiber, sheet, etc. Liver cancer can be treated by injecting the fine particulate form of the inventive composition into liver artery with release of the anticancer agent for a prolonged duration. Additionally, the fine fiberous form of the composition can apply to cancer treatment in various organ by intraperitoneal injection.

The present invention is now illustrated in greater detail with reference to Examples, but it should be understood that the present invention is not deemed to be limited thereto. All the percents are by weight unless otherwise indicated.

EXAMPLE 1

Chitin powder (produced by Shin Nihon Kagaku K.K.), which was prepared by re-acetylating chitosan by reaction with acetic anhydride in a methanol solution, after calcium removal and deproteination, was dissolved in a dimethylacetamide solution containing 8% lithium chloride. The resulting viscous dope was filtered, degassed, and put in a tank. The dope was spouted by means of a gear pump through a nozzle having 600 holes of 0.04 mm in diameter, solidified in an isobutanol bath, and reeled at a speed of 4 m/min to obtain a bundle of fibers of 500 denier. The fiber bundle was cut to a length of about 5 mm, washed with water, and deacetylated in a 29.5% sodium hydroxide aqueous solution at 120° C. for 1 hour. The resulting deacetylated chitin fiber had a DA of 64%.

One gram of the resulting fine fibers was stirred in 400 ml of physiological saline containing 0.1% Cisplatin TM (produced by Nippon Kayaku Co., Ltd.) at 37° C. for 24 hours to obtain a slow-releasing platinum-containing anticancer composition comprising 250 mg of Cisplatin TM bound to the deacetylated chitin.

EXAMPLE 2

Fine fibers of deacetylated chitin having a DA of 40% were prepared in the same manner as in Example 1, except for replacing the 29.5% sodium hydroxide aqueous solution used for deacetylation with a 18% sodium hydroxide aqueous solution.

One gram of the resulting fine fibers was stirred in 400 ml of physiological saline containing 0.1% Carboplatin TM (produced by Bristol Meyers) at 37° C. for 8 hours to obtain a slow-releasing platinum-containing anticancer composition comprising 187 mg of Carboplatin TM bound to the deacetylated chitin.

EXAMPLE 3

Chitin powder (produced by Shin Nihon Kagaku K.K.) was pulverized in a universal ball mill (manufactured by Yamato Kagaku K.K.) to obtain a fine powder having a particle size of not more than 45 μm. The chitin fine powder was deacetylated in a 10% sodium hydroxide aqueous solution at 120° C. for 1 hour to obtain deacetylated chitin fine powder having a DA of 25%.

One gram of the resulting fine powder was stirred in 200 ml of physiological saline containing 0.1% Cisplatin TM at 37° C. for 8 hours to obtain a slow-releasing platinum-containing anticancer composition comprising 110 mg of Cisplatin TM bound to the deacetylated chitin.

TEST EXAMPLE 1

Elution of the platinum-containing anticancer agent from the slow-releasing platinum-containing anticancer compositions obtained in Examples 1 to 3 was tested as follows.

A 0.1 g aliquot of each composition was stirred in 50 ml of a phosphate buffer (pH=6.5) containing 7.5 mg of egg yolk lysozyme at 37° C., and the platinum-containing anticancer agent eluted in the aqueous solution was detected with time by atomic-absorption spectroscopy. The results obtained are shown in Table 1 below.

TABLE 1

| No. | Percent Elution (%) | | | | |
| --- | --- | --- | --- | --- | --- |
| | 0.5 Month | 1 Month | 2 Months | 3 Months | 4 Months |
| Ex. 1 | 5 | 19 | 35 | 52 | 60 |
| Ex. 2 | 9 | 28 | 48 | 70 | 83 |
| Ex. 3 | 15 | 41 | 55 | 78 | 90 |

As is apparent from the results in Table 1, the compositions according to the present invention have excellent slow-releasing properties over a long duration of at least 4 months.

EXAMPLE 4

In a 500 ml wide-mouthed bottle were put 3.0 g of chitin powder (produced by Shin Nippon Kgaku K.K.) and 75 g of a 40% sodium hydroxide aqueous solution. The bottle was placed in a thermostat set at 25° C. and stirred with a magnetic stirrer for 3 hours while maintaining under reduced pressure by means of an aspirator. Then, the bottle was taken out, 225 g of finely crushed ice was put therein, and the content was stirred with a glass rod until the solution became pasty. The bottle was then transferred into a water bath kept at 25° C., and the stirring with a magnetic stirrer was continued for an additional period of 77 hours under normal pressure.

The bottle was transferred in an ice bath, the content was cooled to 5° C. or lower, and 210 g of finely crushed ice was added thereto. While keeping the reaction temperature at 5° C. or lower, the mixture was adjusted to a pH of about 9 by slow dropwise addition of hydrochloric acid and then to a pH of 8.7 with 0.1N hydrochloric acid. The mixture was added dropwise to 5 l of water-containing acetone cooled to 0° C. At this time, cold acetone of 7 times the whole volume of the mixture was separately prepared, and it was added to the reaction system simultaneously with the dropwise addition of the mixture so that the acetone to water ratio of the reaction system was always maintained at 7:1 by volume. After completion of the dropwise addition, the reaction system was allowed to stand for 30 minutes to separate out a flocculent precipitate. The supernatant liquor was removed as much as possible by decantation or the like means. The precipitate was collected on a glass filter (G3) and washed with water-containing acetone until the waste solution produced no turbidity on dropwise addition of a silver nitrate solution. Finally, the precipitate was washed with acetone and lyophilized.

The neutralization and all the operations thereafter were conducted at 5° C. or lower. There was thus obtained 2.28 g (yield: 76%) of water-soluble deacetylated chitin having a DA of 50%.

One gram of the resulting water-soluble chitin was stirred in 500 ml of physiological saline containing 0.1% Cisplatin TM (produced by Nippon Kayaku Co., Ltd.) at 37° C. for 6 hours to obtain a slow-releasing platinum-containing anticancer composition comprising 415 mg of Cisplatin TM in bound form.

TEST EXAMPLE 2

In an ultrafiltration membrane tube ("Seamless Cellulose Tubing" produced by Viskase Sales Corp.) were put 50 ml of a 0.1% aqueous solution of the water-soluble chitin prepared in Example 4 and 2 mg of egg yolk lysozyme, and the tube was agitated in 200 ml of a phosphate buffer (pH=6.5) at 37° C. The platinum-containing anticancer agent eluted in the external phosphate buffer was detected with time by atomic-absorption spectroscopy. The results obtained are shown in Table 2 below.

TABLE 2

| Period (months) | 0.5 | 1 | 2 | 3 | 4 |
| --- | --- | --- | --- | --- | --- |
| Percent Elution (%) | 7 | 29 | 50 | 68 | 80 |

While the invention has been described in detail and with reference to specific examples thereof, it will be apparent to one skilled in the art that various changes and modifications can be made therein without departing from the spirit and scope thereof.

What is claimed is:

1. A pharmaceutical composition consisting essentially of a platinum-containing anticancer agent bound to deacetylated chitin and a pharmaceutically acceptable carrier, wherein the composition has a slow-release property over a duration of at least four months.

2. A pharmaceutical composition as claimed in claim 1, wherein said platinum-containing anticancer agent is at least one member selected from the group consisting of cis-diaminedichloroplatinum (II), cis-diamine(1,1cyclobutanedicarboxylato)platinum (II), (glycolato-0,0')diamineplatinum (II), (R)-(−)-2-aminomethylpyrrolidone(1,1-cyclobutanedicarboxylato)platinum (II), cis-1,1-cyclobutanedicarboxylato(2R)-2-methyl-1,4butanediamineplatinum (II), trans-1-diaminocyclohexaneoxalatoplatinum (II), glycolato-3-aminopyrrolidineplatinum (II), cis-dichloro-trans-dihydroxybisisopropylamineplatinum (IV) and lacto-0,0-1,2-bis-(aminomethyl)cyclobutaneplatinum (II).

3. A pharmaceutical composition as claimed in claim 1, wherein said deacetylated chitin is in a molded form obtained from chitin fibers.

4. A pharmaceutical composition as claimed in claim 1, wherein said composition is in a form selected from a fiber, a powder, a spongy form, a gel, a film, a sheet, or granules.

5. A pharmaceutical composition as claimed in claim 1, wherein said deacetylated chitin has a degree of deacetylation of from 30 to 90%.

6. A pharmaceutical composition as claimed in claim 1, wherein said platinum-containing anticancer agent is present in an amount of from about 5 to about 60% by weight.

7. A method for treating a subject with cancer, comprising administering to a subject in need of treatment a pharmaceutically effective amount of a pharmaceutical composition according to claim 1.

8. A method for preparing a pharmaceutical composition having a slow-release property over a duration of at least four months and consisting essentially of a platinum-containing anticancer agent bound to deacetylated chitin and a pharmaceutically acceptable carrier, comprising (A) contacting a solution of said dissolved platinum-containing anticancer agent with deacetylated chitin;

(B) recovering said platinum-containing anticancer agent bound to deacetylated chitin; and (C) adding the pharmaceutically acceptable carrier to obtain said pharmaceutical composition, wherein said composition does not release said anticancer agent in a saline solution or an aqueous acid solution and wherein said composition releases said anticancer agent in the presence of a lysozyme.

9. A method as claimed in claim 8, wherein said platinum-containing anticancer agent is at least one member selected from the group consisting of cis-diaminedichloroplatinum (II), cis-diamine(1,1-cyclobutanedicarboxylato)platinum (II), (glycolato-0,0')diamineplatinum (II), (R)-(−)-2-aminomethylpyrrolidone(1,1-cyclobutanedicarboxylato)platinum (II), cis-1,1-cyclobutanedicarboxylato(2R)-2-methyl-1,4-butanediamineplatinum (II), trans-1-diaminocyclohexaneoxalatoplatinum (II), glycolato-3-aminopyrrolidineplatinum (II), cis-dichloro-trans-dihydroxybisisopropylamineplatinum (IV) and lacto-0,0-1,2-bis-(aminomethyl)cyclobutaneplatinum (II).

10. A method as claimed in claim 8, wherein said deacetylated chitin is provided in a molded form obtained from chitin fibers.

11. A method as claimed in claim 8, wherein said composition is recovered in a form selected from a fiber, a powder, a spongy form, a gel, a film, a sheet, or granules.

12. A method as claimed in claim 8, wherein said deacetylated chitin has a degree of deacetylation of from about 30 to about 90%.

13. A method as claimed in claim 9, wherein said platinum-containing anticancer agent is present in an amount of from about 5 to about 60% by weight.

* * * * *